(12) United States Patent
Nam et al.

(10) Patent No.: US 7,599,800 B2
(45) Date of Patent: Oct. 6, 2009

(54) APPARATUS AND METHOD FOR CODING GENETIC INFORMATION

(75) Inventors: Yun-sun Nam, Seoul (KR); Byoung-tak Zhang, Seoul (KR); Jang-min O, Gyeonggi-do (KR); Seung-hak Choi, Gyeonggi-do (KR); Kyu-sang Lee, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 11/956,570

(22) Filed: Dec. 14, 2007

(65) Prior Publication Data
US 2008/0097737 A1  Apr. 24, 2008

Related U.S. Application Data

(62) Division of application No. 10/778,807, filed on Feb. 13, 2004, now abandoned.

(30) Foreign Application Priority Data
Feb. 14, 2003 (KR) .................................. 2003-9420

(51) Int. Cl.
*G06F 7/00* (2006.01)
(52) U.S. Cl. .................. 702/19; 702/20; 703/11; 703/13; 707/102; 435/6
(58) Field of Classification Search .............. 702/19, 702/20; 703/11; 707/102; 435/6
See application file for complete search history.

(56) References Cited

U.S. PATENT DOCUMENTS

2004/0006433 A1   1/2004   Robson et al.
2004/0072245 A1   4/2004   Gustafson et al.
2004/0162794 A1   8/2004   Shackleford et al.
2005/0187916 A1   8/2005   Levin et al.

OTHER PUBLICATIONS

Result from Google search of "orthogonal codes" printed Sep. 21, 2006.
Definition of orthogonality from wikipedia (wikipedia.org) printed Sep. 21, 2006.

*Primary Examiner*—Mary K Zeman
(74) *Attorney, Agent, or Firm*—Cantor Colburn LLP

(57) ABSTRACT

Provided are an apparatus and a method for coding genetic information. An aligning unit aligns sample genetic information, wild-type probe genetic information, and mutant-type probe genetic information, based on a mutation position. A code storage unit stores first orthogonal codes assigned to each of bases located at left and right base regions based on the mutation position and second orthogonal codes assigned to a base located at the mutation position. A coding unit creates first code strings and second code strings. The first code strings are created by assigning the first orthogonal codes, sequentially from left to right, to the bases that make the aligned genetic information and adding a flag that represents the presence or absence of a corresponding base on the genetic information to the assigned first orthogonal codes, and the second code strings are created by assigning the second orthogonal codes to the base located at the mutation position and adding a flag that represents the type of the sample genetic information to the assigned second orthogonal codes.

9 Claims, 5 Drawing Sheets

APPARATUS AND METHOD FOR CODING GENETIC INFORMATION

CROSS-REFERENCE TO RELATED APPLICATIONS

This application is a division of U.S. patent application Ser. No. 10/778,807, filed Feb. 13, 2004, which claims priority to Korean Patent Application No. 2003-9420, filed on Feb. 14, 2003, the disclosures of both are incorporated herein by reference in their entirety.

BACKGROUND OF THE INVENTION

1. Field of the Invention

The present invention relates to an apparatus and a method for coding genetic information. More particularly, the present invention relates to an apparatus and a method for coding genetic information to be inputted into a neural network system.

2. Description of the Related Art

A thermodynamic prediction model for DNA hybridization in solutions has been often used to predict the results of DNA chip hybridization. WO01/094611 discloses a method for predicting nucleic acid hybridization thermodynamics. In the disclosed method, hybridization variable information represented by at least one sequence, correction data, and data that represents hybridization conditions are received. Based on the received hybridization variable information, correction data, and hybridization condition data, hybridization thermodynamics including net hybridization thermodynamics are calculated using thermodynamics parameters.

However, since DNA hybridization in solutions differs from that occurring on the surfaces of matters such as chips, a conventional thermodynamic prediction model cannot be used as a prediction model for chips. Also, differences in the protocol cannot be reflected in the thermodynamic prediction model.

SUMMARY OF THE INVENTION

The present invention provides an apparatus and a method for coding genetic information to be inputted into a neural network so as to predict the results of DNA hybridization on various protocols.

According to an aspect of the present invention, there is provided an apparatus for coding genetic information, comprising: a data input unit receiving sample genetic information, wild-type probe genetic information, mutant-type probe genetic information, and a mutation position for each of the genetic information; an aligning unit aligning the sample genetic information, the wild-type probe genetic information, and the mutant-type probe genetic information, based on the mutation position; a code storage unit storing first orthogonal codes assigned to each of bases located at left and right base regions based on the mutation position and second orthogonal codes assigned to a base located at the mutation position; and a coding unit creating first code strings and second code strings, the first code strings being created by assigning the first orthogonal codes, sequentially from left to right, to the bases that make the aligned genetic information and adding a flag that represents the presence or absence of a corresponding base on the genetic information to the assigned first orthogonal codes, and the second code strings being created by assigning the second orthogonal codes to the base located at the mutation position and adding a flag that represents the type of the sample genetic information to the assigned second orthogonal codes.

According to another aspect of the present invention, there is provided a method for coding genetic information, comprising: receiving sample genetic information, wild-type probe genetic information, mutant-type probe genetic information, and a mutation position for each of the genetic information; aligning the sample genetic information, the wild-type probe genetic information, and the mutant-type probe genetic information, based on the mutation position; and creating first code strings and second code strings, the first code strings being created by assigning first orthogonal codes, sequentially from left to right, to bases that make the aligned genetic information and adding a flag that represents the presence or absence of a corresponding base on the genetic information to the assigned first orthogonal codes, and the second code strings being created by assigning second orthogonal codes to a base located at the mutation position and adding a flag that represents the type of the sample genetic information to the assigned second orthogonal codes.

Therefore, a prediction model suitable for current protocols can be designed using existing data, which enables to rapid and accurate prediction of the results of DNA chip hybridization. As a result, time and cost required for selecting probes used on chips can be reduced.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, preferred embodiments of an apparatus and a method for coding genetic information according to the present invention will be described in detail with reference to the accompanying drawings.

Figure 1:
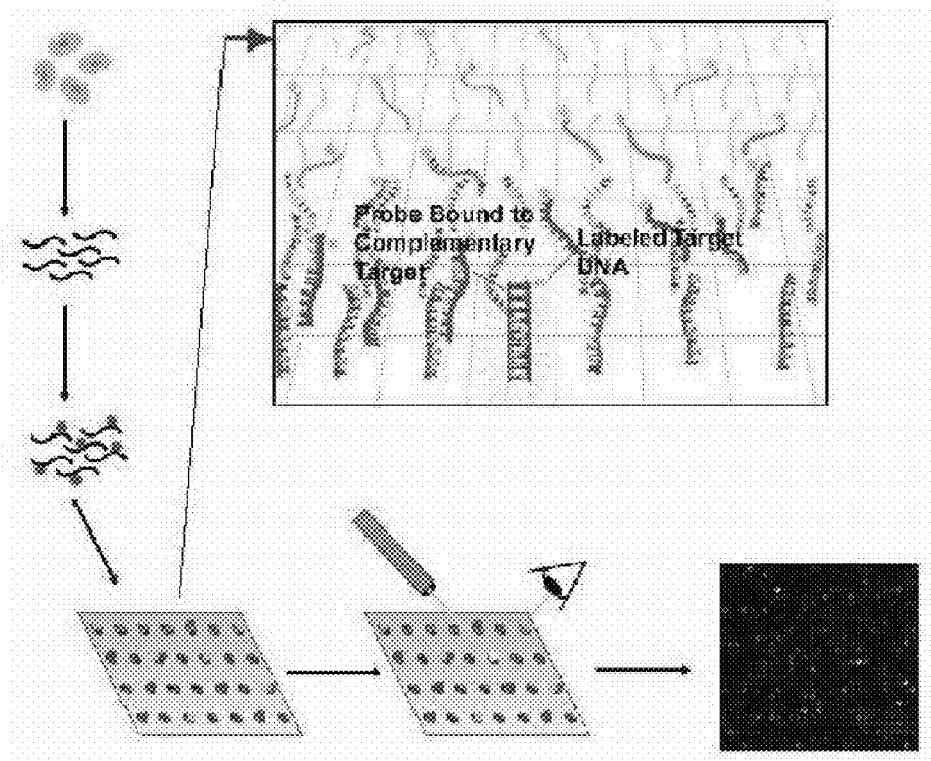
FIG. 1 is a diagram showing the principle of a DNA chip.

FIG. 1 is a diagram showing the principle of DNA chips.

When samples are placed on DNA chips having a plurality of probes, the samples are bound to probes having complementary base sequences. The degree of binding, i.e., hybridization between the probes and the samples, is assessed by the intensity of signal. In such DNA chips, the selection of optimal probes is an important factor that determines the performance of the DNA chips. Generally, probes used on DNA chips are selected by experiments, whereby significant time and cost are incurred.

Figure 2:
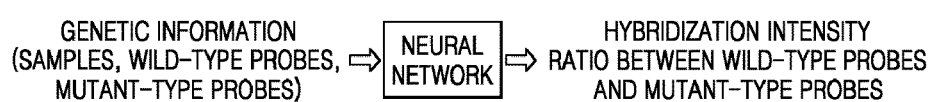
FIG. 2 is a block diagram showing the system of a neural network using coded genetic information according to the present invention as inputs.

The present invention provides an apparatus and a method for coding genetic information to select probes that can be used on DNA chips. The genetic information coding apparatus and method are applied in neural networks using genetic information on samples, wild-type probes, and mutant-type probes as inputs and the hybridization intensity ratios between the wild-type probes and the mutant-type probes or the transformed values as outputs, as shown in FIG. 2. That is, the genetic information coding apparatus of the present invention codes input values to neural networks, i.e., sample genetic information, wild-type probe genetic information, and mutant-type probe genetic information, using codes that reflect genetic information characteristics, and then provides the coded input values to the neural networks. The sample genetic information, the wild-type probe genetic information, and the mutant-type probe genetic information are base sequences consisting of adenine, thymine, guanine, and cytocine.

Figure 3:
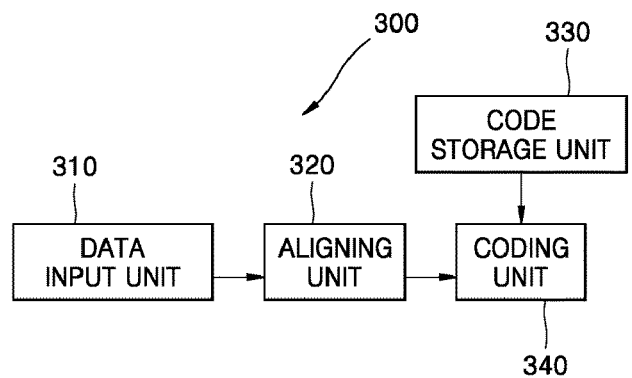
FIG. 3 is a detailed block diagram showing a genetic information coding apparatus according to the present invention.

FIG. 3 is a detailed block diagram showing a genetic information coding apparatus according to the present invention.

Referring to FIG. 3, a genetic information coding apparatus 300 of the present invention includes a data input unit 310, an aligning unit 320, a code storage unit 330, and a coding unit 340.

The data input unit 310 receives sample genetic information, wild-type probe genetic information, and mutant-type probe genetic information, and a mutation position for each of the genetic information, from external devices or users.

Figure 4:
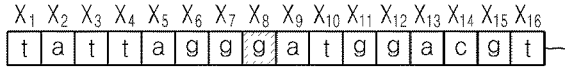
FIG. 4 is genetic information alignment based on received mutation position according to an embodiment of the present invention.

The aligning unit 320 aligns the sample genetic information, the wild-type probe genetic information, and the mutant-type probe genetic information that are received by the data input unit 310, based on a corresponding mutation position on the genetic information. FIG. 4 shows genetic information alignment based on received mutation position. Referring to FIG. 4, the sample genetic information, the wild-type probe genetic information, and the mutant-type probe genetic information are respectively made up of 16, 9, and 8 bases. When position flags, $X_1, X_2, \ldots,$ and $X_{16}$, are sequentially assigned, from left to right, to bases that make the sample genetic information, the mutation position is $X_8$.

The code storage unit 330 stores first orthogonal codes to be assigned to each of bases on upstream (left) and downstream (right) base regions based on mutation position and second orthogonal codes to be assigned to a base located at the mutation position.

The first orthogonal codes are orthogonal to each other and are represented using 4 or 5 bits. Table 1 presents the first orthogonal codes represented using 4 bits and 5 bits.

TABLE 1

| Base | 4 Bit Orthogonal Codes | 5 Bit Orthogonal Codes |
|---|---|---|
| Adenine (A) | 1000 | 10000 |
| Thymine (T) | 0100 | 01000 |
| Guanine (G) | 0010 | 00100 |
| Cytosine (C) | 0001 | 00010 |

The second orthogonal codes are orthogonal to each other and are represented using 12 bits. Since there are 12 types of single nucleotide polymorphisms (SNPs), i.e., A→T, A→G, A→C, T→A, T→G, T→C, G→A, G→T, G→C, C→A, C→T, and C→G, the base located at the mutation position can be represented by 12 bit orthogonal codes. Table 2 presents the second orthogonal codes represented by 12 bits for a base located at mutation position.

TABLE 2

| Mut-ant | Wild | | | |
|---|---|---|---|---|
| | A | T | G | C |
| A | * | 000100000000 | 000000100000 | 000000000100 |
| T | 100000000000 | * | 000000010000 | 000000000010 |
| G | 010000000000 | 000010000000 | * | 000000000001 |
| C | 001000000000 | 000001000000 | 000000001000 | * |

The coding unit 340 creates first code strings by assigning the first orthogonal codes, sequentially from left to right, to bases that make the aligned genetic information, and adding a flag that represents the presence or absence of a corresponding base on the sample genetic information, the wild-type probe genetic information, and the mutant-type probe genetic information, to the assigned first orthogonal codes. Also, the coding unit 340 creates second code strings by assigning the second orthogonal codes to a base located at a mutation position and adding a flag that represent the type of the sample genetic information to the assigned second orthogonal codes. Here, the coding unit 340 codes genetic information by various coding methods according to the relationship with a neural network using the coded results from the coding unit 340 as inputs.

The orthogonal codes presented in Tables 1 and 2 are examples of first orthogonal codes and second orthogonal codes. Original base information and mutation information may be represented by different codes. Further, any other codes except orthogonal codes may be used provided that original base information and mutation information can be identified.

An embodiment of the coding process of the coding unit 340 for aligned genetic information will now be described in detail with reference to FIG. 4. Here, bases that make the genetic information are represented by 4 bit codes.

First, a base located at $X_1$ position is thymine (T). The coding unit 340 searches for the code corresponding to T in the code storage unit 330 and then assigns the searched code value, '0100', to the $X_1$ position. Then, a flag that represents the presence or absence of the T base on each of sample genetic information, wild-type probe genetic information, and mutant-type probe genetic information, is added to the searched code value. Here, the flag is represented using 3 bits, and each bit represents the presence or absence of a corresponding base on each of the sample genetic information, the wild-type probe genetic information, and the mutant-type probe genetic information. Since only the sample genetic information has the T base at $X_1$ position, a flag value, '100' is added. Consequently, the coding unit 340 outputs a code string for the T base located at $X_1$ position, '0100100'. The coding unit 340 creates code strings for the bases located at $X_2$-$X_7$ and $X_9$-$X_{16}$ in the same manner as defined above. The coded results for the rest positions except the mutation position, $X_8$ are summarized as follows:

$X_1$→0100100, $X_2$→1000100, $X_3$→0100100, $X_4$→0100101, $X_5$→1000111,
$X_6$→0010111, $X_7$→0010111, $X_9$→1000111, $X_{10}$→0100111, $X_{11}$→0010111,
$X_{12}$→0010110, $X_{13}$→1000110, $X_{14}$→0001100, $X_{15}$→0010100, $X_{16}$→00100.

The base located at the mutation position is coded using the second orthogonal codes. The wild-type probe genetic information and the mutant-type probe genetic information at the mutation position, $X_8$ are guanine (G) and adenine (A), respectively. The second orthogonal codes for the corresponding base pair are '000000100000'. Then, a flag that represents the type of the sample genetic information is added to the code value assigned for the mutation position. Since the sample genetic information at $X_8$ position is guanine (G), the sample genetic information corresponds to the wild-type probe genetic information. Therefore, '1', representing that the sample genetic information corresponds to the wild-type probe genetic information, is added to the code value, '000000100000'. The coded result is '0000001000001'.

Through the above-described coding procedure, the coding unit 340 outputs the coded results for individual bases located at $X_1$-$X_{16}$ positions. At this time, the coding unit 340 provides mutation position information that represents the mutation position to a neural network, together with the coded results.

Figure 5:
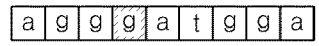
FIG. 5 is genetic information alignment based on received mutation position according to another embodiment of the present invention.

Another embodiment of a coding method that is carried out in the coding unit 340 will now be described with reference to FIG. 5. When genetic information is coded according to the coding method as will be described later, there is no need to separately provide mutation position information to a neural network.

First, the coding unit 340 perceives the distances from a mutation position to the leftmost base and the rightmost base of each of received sample genetic information, wild-type probe genetic information, and mutant-type probe genetic information. Here, the distances from the mutation position to the leftmost base and the rightmost base denote the number of bases. As shown in FIG. 5, provided that the distance from the mutation position to the leftmost base is designated "$R_t$" and the distance from the mutation position to the rightmost base is designated "$R_b$", $R_t$ and $R_b$ for each of the genetic information are as follows:

Sample genetic information: $R_t$=2, $R_b$=9,

Wild-type probe genetic information: $R_t$=5, $R_b$=2,

Mutant-type probe genetic information: $R_t$=3, $R_b$=5.

Next, the coding unit 340 creates a basic base sequence having the distances from the mutation position to the leftmost base and the rightmost base each corresponding to the biggest value, 9, of Rt and Rb values. A basic base sequence for the aligned genetic information as shown in FIG. 5 is made up of 19 bases, and $10^{th}$ base corresponds to the mutation position.

First, the coding unit 340 searches for whether a base is present at $X_1$ position. There are no bases at $X_1$-$X_4$ positions for each of the genetic information. In this regard, in the case of representing the absence of bases at the $X_1$-$X_4$ positions using 4 bit orthogonal codes, the coded result of each of the $X_1$-$X_4$ positions of the basic base sequence is '0000000'. Here, first '0000' is the codes that represent the absence of a base at a corresponding position on all of the received genetic information. These special codes are previously defined in the genetic information coding apparatus of the present invention and a neural network. The coding procedure for $X_5$-$X_{19}$ positions is the same as in the first embodiment, and thus, the detailed description thereof is omitted.

Meanwhile, when 5 bit orthogonal codes are assigned to individual bases of the received genetic information, there is an advantage in that codes that represent the absence of bases at corresponding positions and codes assigned to individual bases located at corresponding positions have an orthogonal relationship. In the application of the above-described coding procedure, it is preferable to limit the number of bases that make the basic base sequence to less than 100. According to the coding procedure as described with reference to FIG. 4, a total of 706 bits is used for the 4-bit coded result output from the genetic information coding apparatus of the present invention. According to the coding procedure as described with reference to FIG. 5, a total of 139 bits is used for the 4-bit coded result.

Figure 6:
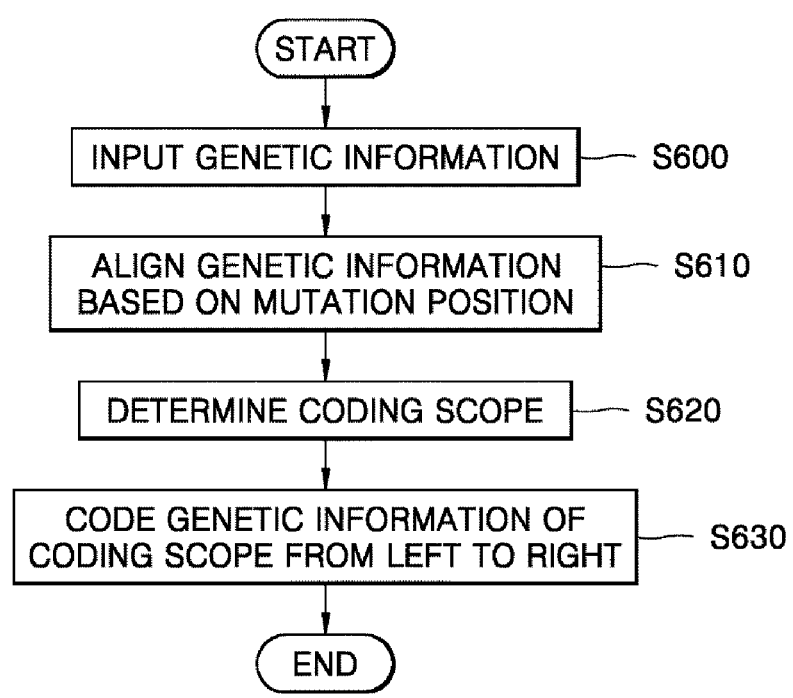
FIG. 6 is a flowchart showing a genetic information coding method according to an embodiment of the present invention.

FIG. 6 is a flowchart showing a genetic information coding method according to an embodiment of the present invention.

Referring to FIGS. 3 and 6, when the data input unit 310 receives genetic information including sample genetic information, wild-type probe genetic information, and mutant-type probe genetic information, and a mutation position for each of the genetic information (step S600), the aligning unit 320 aligns the genetic information based on the mutation position (step S610). The coding unit 340 determines a coding scope by perceiving the positions of the leftmost base and the rightmost base of each of the aligned genetic information based on the mutation position (step S620). The coding unit 340 codes, sequentially from left to right, the bases within the coding scope determined based on the leftmost base and the rightmost base perceived on each of the genetic information. The coding procedure of the coding unit 340 is the same as described above, and thus, the detailed description thereof is omitted.

The genetic information coding apparatus of the present invention provides the coded results of genetic information on samples and probes to a neural network. The neural network perceives genetic information based on the coded values received from the genetic information coding apparatus and then outputs the hybridization intensity ratios between wild-type probes and mutant-type probes or the transformed values.

If the log values of the hybridization intensity ratios between wild-type probes and mutant-type probes are scaled from −1 to 1, the output values, y of the neural network are represented by following Equation 1:

$$y = \frac{2}{\max - \min} \log \frac{wp}{mp} - \frac{\max + \min}{\max - \min} \quad (1)$$

where, wp is the hybridization intensity of wild-type probes, mp is the hybridization intensity of mutant-type probes, max is the maximum log value of the hybridization intensity ratios between wild-type probes and mutant-type probes, and min is the minimum log value of the hybridization intensity ratios between wild-type probes and mutant-type probes.

Figure 7:
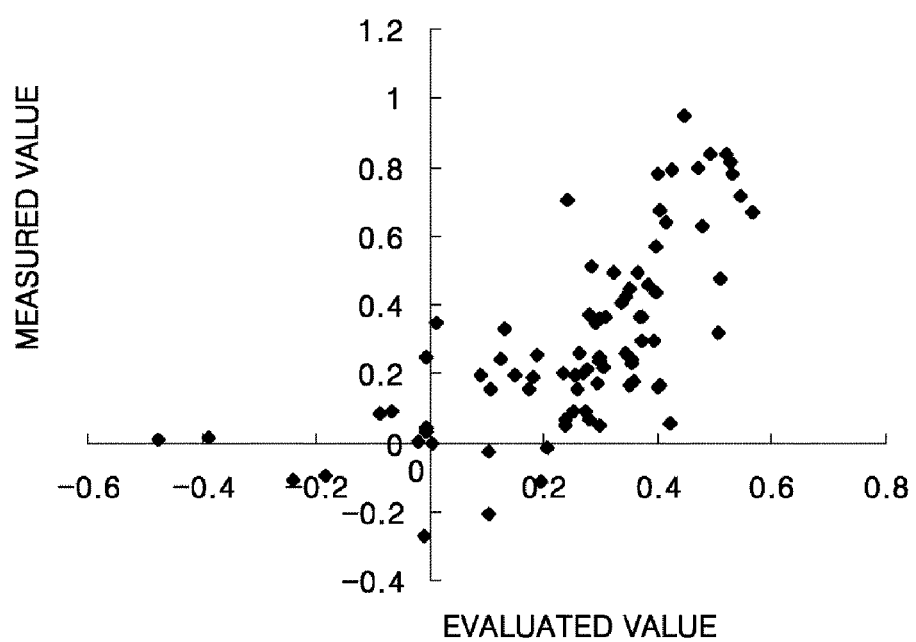
FIG. 7 is a graph showing the test results of a trained neural network on 82 test sets.

A neural network model that outputs effective results by training a neural network based on the coded results received from the genetic information coding apparatus of the present invention can be selected. For example, we apply the present invention to a set of 2952 data, 2152 for the training data set and 800 for the validation data set are used as learning data of the neural network. The neural network uses a batch learning according to a conjugate gradient algorithm. To prevent excessive learning, the neural network is trained using the training data sets until maximum epoch is reached. After an error history for the validation data sets is analyzed, recurrent training is carried out until the epoch which exhibits the lowest error rate is reached. Thereafter, various neural network models are designed by changing the number of hidden layers and the number of neurons. A model that exhibits the lowest error rate for the validation data sets is selected as a final neural network model. The final neural network model has 0.168036 of root mean square error (RMSE) for the validation data sets. FIG. 7 shows the test results of a trained neural network on 82 test data sets. Here, the RMSE of the neural network is 0.200939.

According to the genetic information coding apparatus and method of the present invention, genetic information to be inputted into a neural network is coded based on genetic information characteristics. Therefore, a prediction model suitable for current protocols can be designed using existing data, which enables to rapid and accurate prediction of the results of DNA chip hybridization.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for predicting probe hybridization to a DNA chip, comprising:

receiving sample genetic information, wild-type probe genetic information, mutant-type probe genetic information, and a mutation position for each type of genetic information from a user of a DNA chip;

aligning the sample genetic information, the wild-type probe genetic information, and the mutant-type probe genetic information at the mutation position in each type of genetic information;

coding the aligned genetic information by creating first code strings and second code strings, the first code strings being created by assigning first orthogonal codes, sequentially from left to right excluding the mutation position, to bases in the aligned genetic information and adding a flag to the assigned first orthogonal codes that represents the presence or absence of a corresponding base in each type of genetic information, and the second code strings being created by assigning second orthogonal codes to a base located at the mutation position and adding a flag to the assigned second orthogonal codes that represents whether the base located at the mutation position of the sample genetic information is wild-type or mutant-type;

inputting the coded aligned genetic information into a neural network trained to predict results of hybridization to the DNA chip; and outputting from the neural network the hybridization intensity ratios between wild-type probes and mutant-type probes, or the transformed values thereof, to the user of the DNA chip.

2. The method of claim 1, wherein the first orthogonal codes are 4 bit codes that are orthogonal to each other, and the flag added to the assigned first orthogonal codes is made up of a set of subflags, each of which has 1 bit that corresponds to each type of genetic information, and wherein when the corresponding base is present in the genetic information, the value of each of the subflags is '1', and when the corresponding base is absent from the genetic information, the value of each of the subflags is '0'.

3. The method of claim 1, wherein the first orthogonal codes are 5 bit codes that are orthogonal to each other, and the flag added to the assigned first orthogonal codes is made up of a set of subflags, each of which has 1 bit that corresponds to each type of genetic information, and wherein when the corresponding base is present in the genetic information, the value of each of the subflags is '1', and when the corresponding base is absent from the genetic information, the value of each of the subflags is '0'.

4. The method of claim 1, wherein the second orthogonal codes are 12 bit orthogonal code strings that represent pairs of bases that are the wild-type probe genetic information and the mutant-type probe genetic information at the mutation position.

5. The method of claim 1, wherein creating the first code strings and the second code strings comprises:

determining distances from the mutation position to the leftmost base and the rightmost base for each type of genetic information;

creating a basic base sequence having distances from the mutation position to the leftmost base and the rightmost base each corresponding to the biggest value among the determined distances; and coding bases of the basic base sequence sequentially from left to right.

6. The method of claim 5, wherein in creating the first code strings and the second code strings, the first code strings being created in such a way that at the time of coding the left and right base regions based on the mutation position, when bases are absent from the genetic information corresponding to base positions of the basic base sequence, third codes that represent the absence of the bases in the genetic information are assigned to the bases, and when the bases are present in the genetic information corresponding to the base positions of the basic base sequence, the first orthogonal codes with predetermined sizes are assigned to the bases, and the flag that represents the presence or absence of the corresponding base in the genetic information is assigned to the assigned first orthogonal codes or the assigned third codes; and the second code strings being created in such a way that the second orthogonal codes with predetermined sizes are assigned to the base located at the mutation position and the flag that represents whether the base at the mutation position of the sample genetic information is wild-type or mutant-type is added to the assigned second orthogonal codes.

7. The method of claim 6, wherein the first orthogonal codes are 4 bit codes that are orthogonal to each other, the third codes are '0000', and the flag added to the assigned first orthogonal codes or the assigned third codes is made up of a set of subflags, each of which has 1 bit that corresponds to each type of genetic information, and wherein when the corresponding base is present in the genetic information, the value of each of the subflags is '1', and when the corresponding base is absent from the genetic information, the value of each of the subflags is '0'.

8. The method of claim 6, wherein the first orthogonal codes and the third codes are 5 bit codes that are orthogonal to each other, and the flag added to the assigned first orthogonal codes or the assigned third codes is made up of a set of subflags, each of which has 1 bit that corresponds to each type of genetic information, and wherein when the corresponding base is present in the genetic information, the value of each of the subflags is '1', and when the corresponding base is absent from the genetic information, the value of each of the subflags is '0'.

9. The method of claim 6, wherein the second orthogonal codes are 12 bit orthogonal code strings that represent pairs of bases that are the wild-type probe genetic information and the mutant-type probe genetic information at the mutation position.

* * * * *

SEQUENCE LISTING

<160> NUMBER OF SEQ ID NOS: 2

<210> SEQ ID NO 1
<211> LENGTH: 16
<212> TYPE: DNA
<213> ORGANISM: Artificial Sequence
<220> FEATURE:
<223> OTHER INFORMATION: Exemplary Sequence

<400> SEQUENCE: 1
tattagggat ggacgt                                               16

<210> SEQ ID NO 2
<211> LENGTH: 12
<212> TYPE: DNA
<213> ORGANISM: Artificial Sequence
<220> FEATURE:
<223> OTHER INFORMATION: Exemplary sequence

<400> SEQUENCE: 2
tattagggat gg                                                   12